(12) United States Patent
Hong et al.

(10) Patent No.: US 8,877,734 B2
(45) Date of Patent: Nov. 4, 2014

(54) SELENY-METHYLURACIL COMPOUNDS, RADIOSENSITIZER AND PHARMACEUTICAL COMPOSITION USING THEM

(75) Inventors: In Seok Hong, Daejeon (KR); Sung Hee Hong, Seoul (KR); Marc M. Greenberg, Baltimore, MD (US)

(73) Assignee: Kongju National University Industry-University Cooperation Foundation, Gongju-si (KR)

( * ) Notice: Subject to any disclaimer, the term of this patent is extended or adjusted under 35 U.S.C. 154(b) by 0 days.

(21) Appl. No.: 13/878,711

(22) PCT Filed: Dec. 23, 2010

(86) PCT No.: PCT/KR2010/009263
§ 371 (c)(1),
(2), (4) Date: May 3, 2013

(87) PCT Pub. No.: WO2012/050264
PCT Pub. Date: Apr. 19, 2012

(65) Prior Publication Data
US 2013/0211067 A1   Aug. 15, 2013

(30) Foreign Application Priority Data

Oct. 11, 2010   (KR) ........................ 10-2010-0098596

(51) Int. Cl.
*A61K 31/70* (2006.01)
*A61K 31/505* (2006.01)
*C07H 19/00* (2006.01)
*C07D 239/02* (2006.01)
*A61K 41/00* (2006.01)
*C07H 19/073* (2006.01)
*C07H 19/06* (2006.01)

(52) U.S. Cl.
CPC .......... *A61K 41/0038* (2013.01); *C07H 19/073* (2013.01); *C07H 19/06* (2013.01)
USPC ........... 514/50; 514/269; 536/28.54; 544/298

(58) Field of Classification Search
None
See application file for complete search history.

(56) References Cited

U.S. PATENT DOCUMENTS 6,590,107 B1   7/2003   Schinazi et al.

OTHER PUBLICATIONS

Kim et al., Bioorganic and Medicinal chemistry Letters, 18 (2008) 5054-5057.*
Hong et al., Organic Letters, 2004, vol. 6(26) 5011-5013.*
Robert W. Buckheit Jr., "The structure-activity relationships of 2,4(1H,3H)-pyrimidinedione derivatives as potent HIV type 1 and type 2 inhibitors", Antiviral Chemistry & Chemotherapy, 2007, pp. 259-275, vol. 18.
G. Mazumder, "1-(Ethoxymethyl)-6-(phenylselenyl)-5-ethyl uracil: a nucleoside analog", Journal of Chemical Crystallography, 1999, pp. 837-839, vol. 29, No. 7.
Keri A. Tallman et al., "Oxygen-Dependent DNA Damage Amplification Involving 5,6-Dihydroythymidin-5-yl in a Structurally Minimal System", J. Am. Chem. Soc., 2001, pp. 5181-5187, vol. 123.
International Searching Authority International Search Report for PCT/KR2010/009263 dated Dec. 12, 2011.

* cited by examiner

*Primary Examiner* — Traviss C McIntosh, III
(74) *Attorney, Agent, or Firm* — Sughrue Mion, PLLC

(57) ABSTRACT

Provided are novel selenyl-methyluracil compounds and a pharmaceutical composition for enhancing the effect of radiation treatment. The composition contains at least one compound selected from the group consisting of the selenyl-methyluracil compounds or pharmaceutically acceptable salts thereof, as an active ingredient.

14 Claims, 3 Drawing Sheets

SELENY-METHYLURACIL COMPOUNDS, RADIOSENSITIZER AND PHARMACEUTICAL COMPOSITION USING THEM

CROSS REFERENCE TO RELATED APPLICATIONS

This application is a National Stage of International Application No. PCT/KR2010/009263 filed Dec. 23, 2010, claiming priority based on Korean Patent Application No. 10-2010-0098596 filed Oct. 11, 2010, the contents of all of which are incorporated herein by reference in their entirety.

TECHNICAL FIELD

The present invention relates to novel selenyl-methyluracil compounds and a pharmaceutical composition for enhancing the effect of radiotherapy comprising the same.

BACKGROUND ART

Methods for treating malignant tumors may be generally classified into surgical methods, chemotherapy and radiotherapy (radiation therapy). About 35% of all cancer patients in South-Korea and about 50% thereof in US receive some type of radiotherapy, at present, and the number of domestic patients who need to receive radiotherapy is increasing every year. Under this circumstance, the importance of radiotherapy in cancer treatment is presently increasing. Radiotherapy has been known as an essential treatment method for various types of cancer, however, it also has some problems such as resistance to radiation built in cancer cells, low efficiency against solid cancers, damages in normal tissue when high-dose of radiation is applied, or the like, resulting in lowering the efficiency in cancer treatment. For obtaining high anti-tumor effect, chemoradiotherapy, i.e., the combined therapy simultaneously using chemotherapy agents and radiation, has been introduced as a general therapy, and it has also been reported that it gives better results than chemotherapy or radiotherapy alone (Nishimura, Y., Int. J. Clin. Oncol., 2004, 9, 414). It was reported, for instance that in head and neck cancer, the combination of carboplatin/fluorouracil and radiation treatment (Calais et al., J. Natl. Cancer Inst. 1999, 91, 2081) and another combination of cisplatin and radiation treatment (Jeremic et al., J. Clin. Oncol. 2000, 18, 1458), and the combination of fluorouracil and radiation treatment in pancreatic cancer (Moertel, et al., Cancer 1981, 48, 1705) etc. significantly extended the surviving period in patients, as compared when radiotherapy was applied alone.

Many approaches to develop radiosensitizers that can reduce the radiation dose so as to reduce side effects without decreasing the efficacy of radiotherapy have been made. For example, compounds such as misonidazole and etanidazole, etc. were developed from nitroimidazole derivatives which are known as a radiosensitizer. However, these compounds were not successfully commercialized for practical use due to the fact that they have strong neurotoxicity when used at the effective amount for radiosensitizing effect.

DISCLOSURE OF INVENTION

Technical Problem

An object of the present invention is to provide novel selenyl-methyluracil derivatives.

Another object of the present invention is to provide a pharmaceutical composition for enhancing the effect of radiotherapy comprising the selenyl-methyluracil compound or pharmaceutically acceptable salts thereof as an active ingredient.

Still another object of the present invention is to provide a pharmaceutical composition for treating cancers, which comprises the selenyl-methyluracil compound or pharmaceutically acceptable salts thereof as an active ingredient.

Solution to Problem

In order to resolve the above-mentioned problems in the prior arts, the present inventors have conducted an extensive research and finally completed the present invention by successfully synthesizing novel selenyl-methyluracil compounds from a mother compound, 5-phenylselenyl methyluridine monomers which were reported to form complementary covalent bonds between DNA strands in a DNA double strand upon application of UV or radiation (Hong et al., J. Amer. Chem. Soc. 2005, 127, 3692; Hong et al., J. Amer. Chem. Soc. 2006, 128, 2230) as a mother compound. The novel compounds of the present invention, which have not been disclosed in any other publications, have been confirmed to have significantly low cytotoxicity as compared to well-known radiosensitizers such as taxol and cisplatin, while exerting great effects when combined with a radiation treatment.

In order to achieve the objects of the present invention, selenyl-methyuracil compounds represented by the following chemical formula 1 are provided:

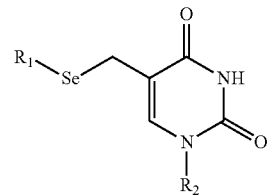

[Chemical formula 1]

[In the above chemical formula 1,
$R_1$ is C1-C8 alkyl, C2-C7 alkenyl, C3-C6 cycloalkyl or C6-C12 aryl; $R_2$ is C1-C8 alkyl, carboxy(C1-C6)alkyl, carboxy(C6-C12)aryl, or pentose or hexose; the alkyl, alkenyl, cycloalkyl or aryl group of $R_1$ may be further substituted with hydrogen, halogen, C1-C6 alkyl, C2-C7 alkenyl, C2-C7 alkylnyl, cyano, halogen, C1-C6 alkoxy, —$NR_{11}R_{12}$, carboxyl, nitro or hydroxyl group; wherein $R_{11}$ and $R_{12}$, being independent to each other, are hydrogen, C1-C6 alkyl, C6-C12 aryl or C3-C12 heteroaryl group containing at least one hetero atom selected from N, O and S; provided that the case that $R_1$ is phenyl and $R_2$ is

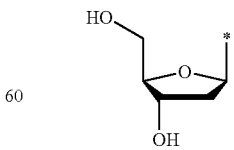

is excluded].

More specifically, the present invention provides selenyl-methyluracil compounds represented by the following chemical formula 2:

[Chemical formula 2]

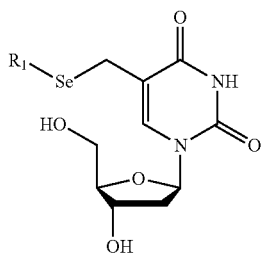

[In the above chemical formula 2, $R_1$ is C1-C6 alkyl, C2-C7 alkenyl, or C3-C6 cycloalkyl; the alkyl, alkenyl or cycloalkyl group of $R_1$ may be further substituted with hydrogen, halogen, C1-C6 alkyl, C2-C7 alkenyl, C2-C7 alkylnyl, cyano, halogens, C1-C6 alkoxy, $-NR_{11}R_{12}$, carboxyl, nitro or hydroxyl group; wherein $R_{11}$ and $R_{12}$, being independent to each other, are hydrogen, C1-C6 alkyl, C6-C12 aryl or C3-C12 heteroaryl group containing at least one heteroatom selected from N, O and S].

The compounds of the chemical formula 2 may be exemplified by the following specific compounds, however these compounds by no means limit the scope of the present invention.

1

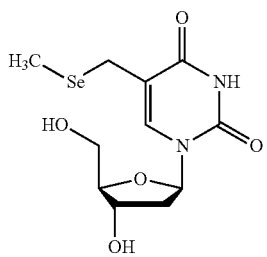

2

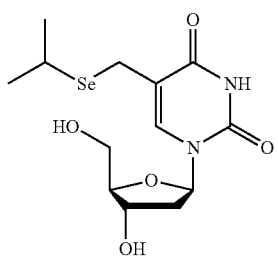

3

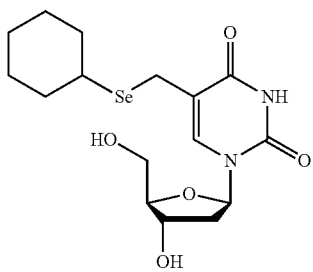

4

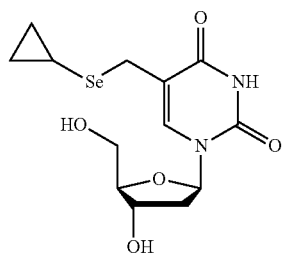

5

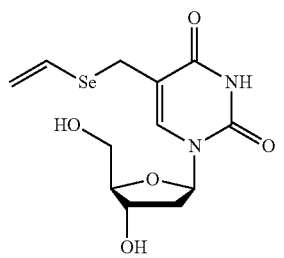

6

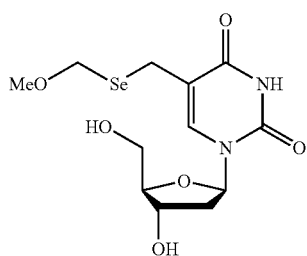

'Alkyl', 'alkoxy' and other substituted compound comprising 'alkyl' moiety as described in the present specification include the form of a straight or branched chain.

In another aspect, the present invention provides a pharmaceutical composition for enhancing the effect of radiotherapy which comprises selenyl-methyluracil compounds represented by the following chemical formula 3 or pharmaceutically acceptable salts thereof, as an active ingredient:

[Chemical formula 3]

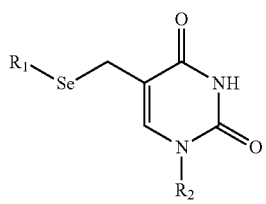

[In the above chemical formula 3, $R_1$ is C1-C8 alkyl, C2-C7 alkenyl, C3-C6 cycloalkyl, C6-C12 aryl or C3-C12 heteroaryl group containing at least one heteroatom selected from N, O and S; $R_2$ is C1-C8 alkyl, carboxy(C1-C6)alkyl, carboxy(C6-C12)aryl, or pentose or hexose; the alkyl, alkenyl, cycloalkyl, aryl or heteroaryl group of $R_1$ may be further substituted with hydrogen, halogen, C1-C6 alkyl, C2-C7 alkenyl, C2-C7 alkylnyl, cyano, halogen, C1-C6 alkoxy, $-NR_{11}R_{12}$, carboxyl, nitro or hydroxyl group; wherein $R_{11}$ and $R_{12}$, being independent to each other, are hydrogen, C1-C6 alkyl, C6-C12 aryl or C3-C12 heteroaryl group containing at least one heteroatom selected from N, O and S].

The present invention further provides a pharmaceutical composition for enhancing the effect of radiotherapy which comprises selenyl-methyluracil compounds represented by the following chemical formulas 4 and 5, or pharmaceutically acceptable salts thereof as an active ingredient:

[Chemical formula 4]

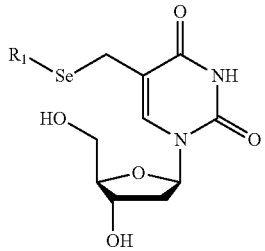

[Chemical formula 5]

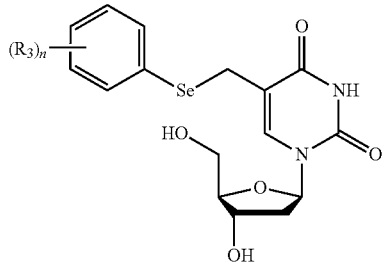

[In the above chemical formulas 4 and 5,

R$_1$ is C1-C6 alkyl, C2-C7 alkenyl or C3-C6 cycloalkyl; the alkyl, alkenyl or cycloalkyl group of R$_1$ may be further substituted with hydrogen, halogen, C1-C6 alkyl, C2-C7 alkenyl, C2-C7 alkylnyl, cyano, halogen, C1-C6 alkoxy, —NR$_{11}$R$_{12}$, carboxyl, nitro or hydroxyl group; wherein R$_{11}$ and R$_{12}$, being independent to each other, are hydrogen, C1-C6 alkyl, C6-C12 aryl or C3-C12 heteroaryl group containing at least one heteroatom selected from N, O and S; R$_3$ is hydrogen, halogen, C1-C6 alkyl, C2-C7 alkenyl, C2-C7 alkynyl, cyano, halogen, C1-C6 alkoxy, —NR$_{21}$R$_{22}$, carboxyl, nitro or hydroxyl group; wherein R$_{21}$ and R$_{22}$, being independent to each other, are hydrogen, C1-C6 alkyl, C6-C12 aryl or C3-C12 heteroaryl group containing at least one heteroatom selected from N, O and S; and n is an integer of 1 to 5].

The compounds of the chemical formulas 4 and 5 may be exemplified by the following specific compounds; however these compounds by no means limit the scope of the present invention

1

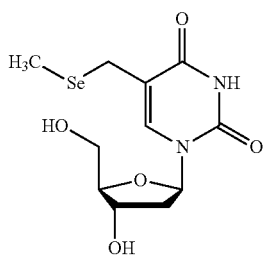

2

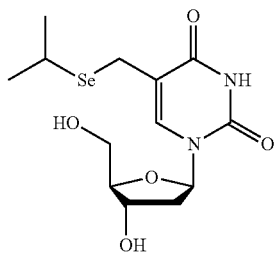

3

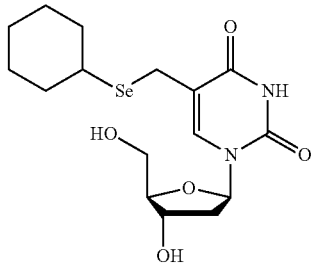

4

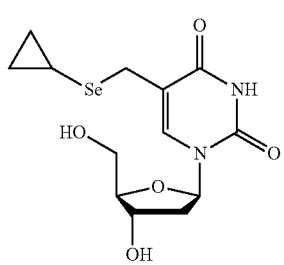

5

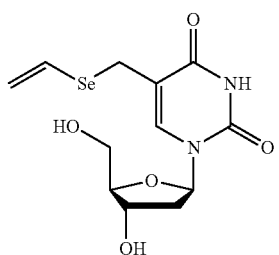

6

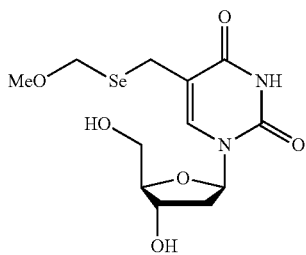

7

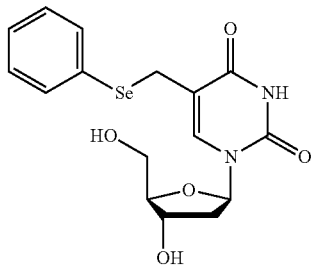

8

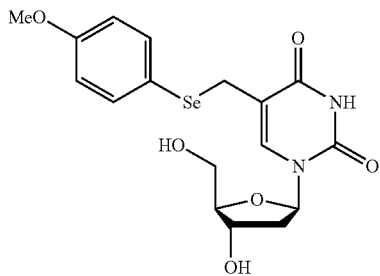

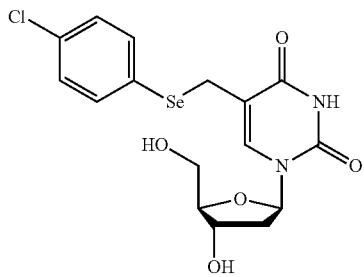

The present invention further provides a pharmaceutical compound for cancer treatment, which comprises selenyl-methyluracil compounds represented by the following chemical formula 6 or pharmaceutically acceptable salts thereof as an active ingredient:

[Chemical formula 6]

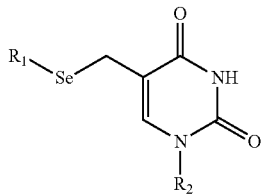

[In the above chemical formula 6, $R_1$ is C1-C8 alkyl, C2-C7 alkenyl, C3-C6 cycloalkyl, C6-C12 aryl or C3-C12 heteroaryl group containing at least one heteroatom selected from N, O and S; $R_2$ refers to C1-C8 alkyl, carboxy(C1-C6)alkyl, carboxy(C6~C12)aryl, or pentose or hexose; the alkyl, alkenyl, cycloalkyl, aryl or heteroaryl group of $R_1$ may be further substituted with hydrogen, halogen, C1-C6 alkyl, C2-C7 alkenyl, C2-C7 alkylnyl, cyano, halogen, C1-C6 alkoxy, —$NR_{11}R_{12}$, carboxyl, nitro or hydroxyl group; wherein $R_{11}$ and $R_{12}$, being independent to each other, are hydrogen, C1-C6 alkyl, C6-C12 aryl or C3-C12 heteroaryl group containing at least one heteroatom selected from N, O and S].

The cancer diseases to which the pharmaceutical composition having a selenyl-methyluracil compound or pharmaceutically acceptable salts thereof according to the present invention as an active ingredient, for cancer treatment, include prostate cancer, breast cancer, brain tumor, thyroid cancer, pancreatic cancer, pituitary cancer, cervical cancer, uterine cancer, ovarian cancer, esophageal cancer, gastric cancer, colon cancer, rectal cancer, liver cancer, gallbladder cancer, lung cancer, oral cavity cancer, skin cancer, renal cancer, leukemia, lymphoma and myeloma.

The present invention further provides a pharmaceutical composition for cancer treatment, which comprises a selenyl-methyluracil compound represented by the following chemical formulas 7 and 8, or pharmaceutically acceptable salts thereof:

[Chemical formula 7]

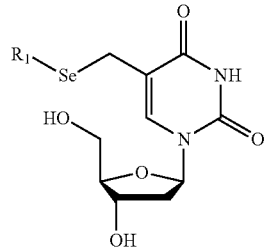

[Chemical formula 8]

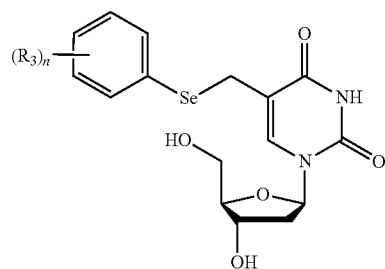

[In the above chemical formulas 7 and 8, $R_1$ is C1-C6 alkyl, C2-C7 alkenyl or C3-C6 cycloalkyl; the alkyl, alkenyl or cycloalkyl group of $R_1$ may be further substituted with hydrogen, halogen, C1-C6 alkyl, C2-C7 alkenyl, C2-C7 alkylnyl, cyano, halogen, C1-C6 alkoxy, —$NR_{11}R_{12}$, carboxyl, nitro or hydroxyl group; wherein $R_{11}$ and $R_{12}$, being independent to each other, are hydrogen, C1-C6 alkyl, C6-C12 aryl or C3-C12 heteroaryl group containing at least one heteroatom selected from N, O and S; $R_3$ is hydrogen, halogen, C1-C6 alkyl, C2-C7 alkenyl, C2-C7 alkynyl, cyano, halogen, C1-C6 alkoxy, —$NR_{21}R_{22}$, carboxyl, nitro or hydroxyl group; $R_{21}$ and $R_{22}$, being independent to each other, hydrogen, C1-C6 alkyl, C6-C12 aryl or C3-C12 heteroaryl group containing at least one heteroatom selected from N, O and S; and n is an integer of 1 to 5].

The compounds of the chemical formulas 7 and 8 may be exemplified by the following specific compounds, however these compounds by no means limit the scope of the present invention.

1

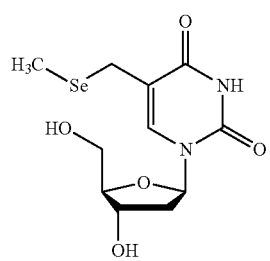

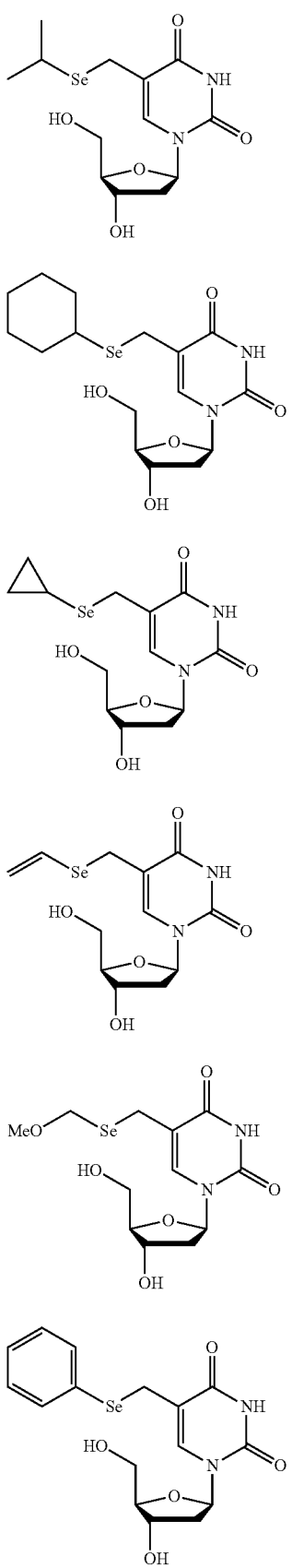
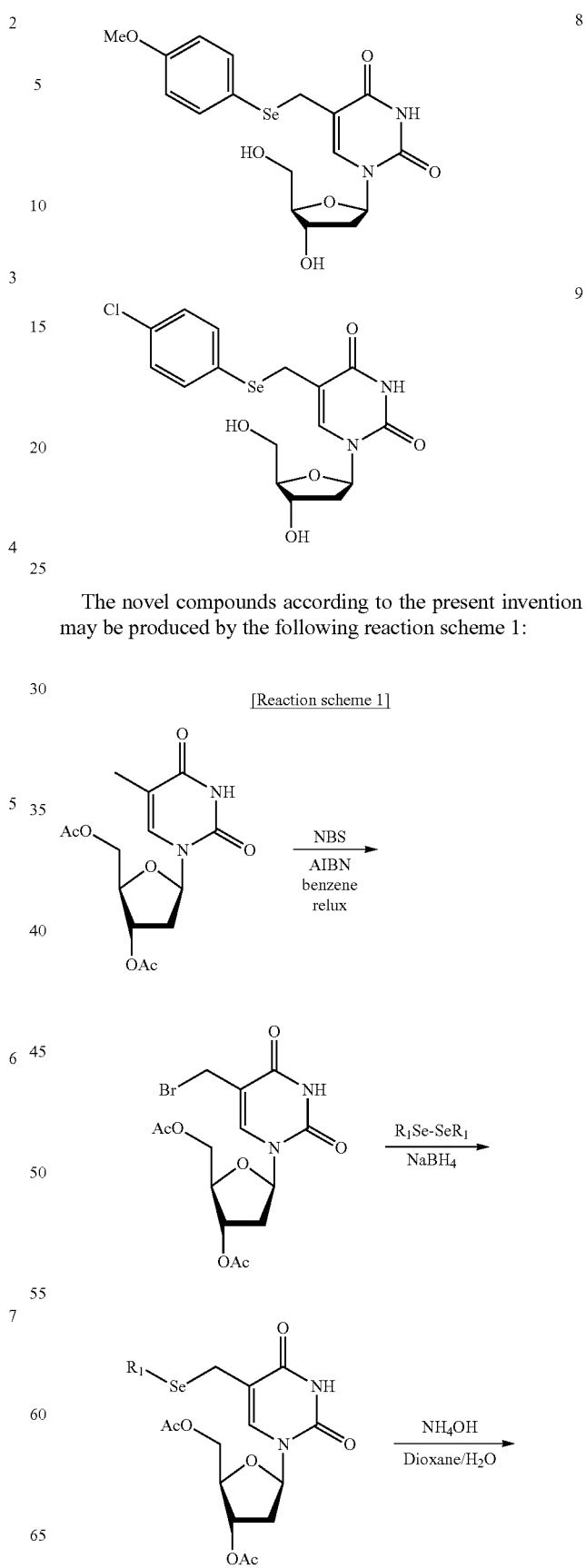
The novel compounds according to the present invention may be produced by the following reaction scheme 1:
[Reaction scheme 1]

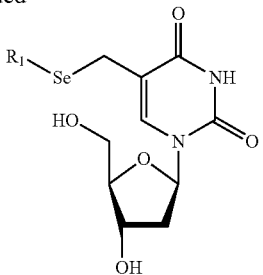

[In the above reaction scheme 1, $R_1$ has the same meaning as the definition thereof in the chemical formula 1]

The pharmaceutical composition for enhancing the effect of radiotherapy used in the present invention relates to a substance which is used together with anticancer radiation treatment and thus can increase the sensitivity of cancer cells to radiation, resulting in improving the radiation treatment efficiency. In other words, the substance is used together with radiation treatment for treating cancer so as to enhance the sensitivity of the cancer cells to radiation, thereby showing the effect of killing or inhibiting cancer cells, and it is also referred as a radiosensitizer. Good radiosensitizers have low cytotoxicity as the compound per se, thereby having no significant effect on normal cells, while their effect on cancer cells can be greatly increased only when combined with radiation.

The pharmaceutically acceptable salts used herein, refers to any salt of the selenyl-methyluracil compound. Some examples of the pharmaceutically acceptable salts include, for instance, acid addition salts such as hydrochloric acid, sulfuric acid, phosphoric acid, citric acid, maleic acid, fumaric acid, malic acid, acetic acid and benzoic acid salts, etc., and basic salts such as salts of sodium, potassium, calcium, ammonia and methylamine, etc., without any intention to limit the present invention with the exemplified salts.

The composition for enhancing the effect of radiation treatment according to the present invention may contain additives for extending the shelf life or preserving the effectiveness, such as preservatives, antioxidants, wetting agents, emulsifiers, burring agents, non-ionic surfactants and the like. Suitable examples of such preservatives, antioxidants, wetting agents, etc. are well-known in this field of art where the present invention pertains. Further, the composition for enhancing the effect of radiation treatment according to the present invention may be formulated in various forms, such as liquid solution, suspension, syrup, tablet, coated tablet, pill, granule, capsule, ointment, injection, suppository and the like.

The composition for enhancing the effect of radiation treatment according to the present invention is applied in combination with radiation treatment, and may be administered before or after the radiation treatment. The amount being administered of the present composition may be variously determined by medical professionals on the basis of the amount of active ingredients in a composition, seriousness of diseases, patient's weight, a dosage form, administration route and administration period, but generally the dosage amount of 0.1-100 mg/kg is preferably used. The formulation of the present invention may be administered once a day, or as being divided into 2-4 times per day.

The composition for enhancing the effect of radiation treatment according to the present invention may be orally or parenterally administered to mammals including human. Any administration methods or routes well-known by a skilled person in the art may be used for the present invention, for example such as intravenously, intradermally, intraarterially, intraperitoneally, intralesionally, intracranially, intraarticularly, intraprostatically, intrapleurally, intratracheally, intranasally, intravitreally, intravaginally, intrarectally, locally, intratumorally, intramuscularly, subcutaneously, subconjunctivally, intravesiclarly, transmucosally, intrapericardially, intraumbilically, intraocularly, orally, regionally, and topically, and; by inhalement, injection, infusion, continuous infusion, direct local bath perfusion to target cells, catheter or washing.

The term cancer as used herein, refers to uncontrolled growth, division or propagation of abnormal cells. The cancers which can be effectively treated by the composition described in the present invention may include, without being limited to these, prostate cancer, breast cancer, brain tumor, thyroid cancer, pancreatic cancer, pituitary cancer, cervical cancer, uterine cancer, ovarian cancer, esophageal cancer, gastric cancer, colon cancer, rectal cancer, liver cancer, gallbladder cancer, lung cancer, oral cavity cancer, skin cancer, renal cancer, leukemia, lymphoma and myeloma.

Advantageous Effects of Invention

The selenyl-methyluracil compounds according to the present invention can enhance the effects of radiotherapy, while having low cytotoxicity, thereby being possible to be used as a radiosentizer. Specifically, 5-methylselenyl-methyldeoxyuridine and 5-phenylselenyl-methyldeoxyuridine are synthesized by the present invention are nucleoside derivatives present in a human body which can kill cancerous cells by being applied alone or in combination with radiotherapy, thereby being possible to maximize the efficiency of cancer treatment.

BEST MODE FOR CARRYING OUT THE INVENTION

Figure 1:
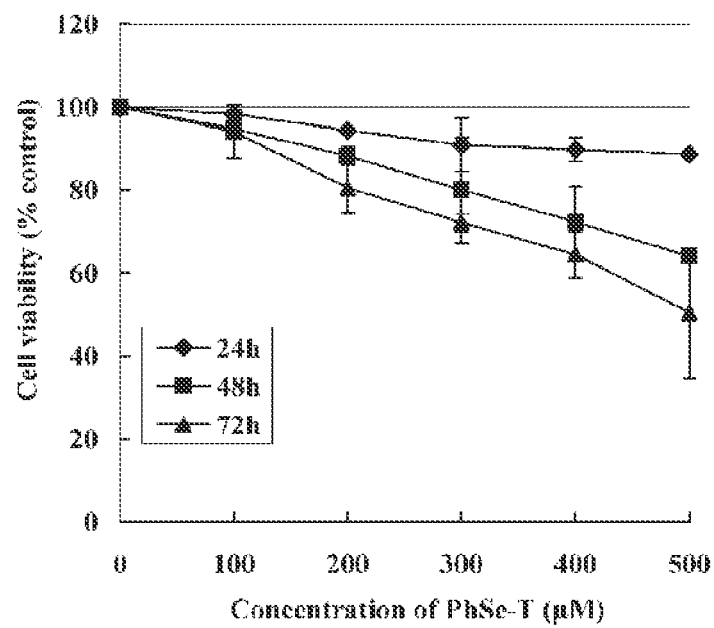
FIG. 1 is a plot showing the viability of lung cancer cell (H460) when treated by PhSe-T according to the present invention.

Hereinafter, the present invention is further illustrated by way of the following examples. However, these examples are provided only to help understand the constitution and effects of the present invention, and by no means limiting the scope of the present invention.

Preparation Example 1

Preparation of Compound A

A 250 mL-volume round bottom flask was charged with 3',5'-bis-O-acetyl thymidine (3 g, 9.19 mmol), N-bromosuccimide (3.2 g, 18.0 mmol), and a radical initiator, AIBN (Azobis Isobutyronitrile, 150 mg), and 100 mL of benzene solvent was further added thereto. The reaction solution was refluxed for two and half hours, and then the transparent reaction solution was changed to an orange color. The reaction was stopped by cooling the reaction solution, and the solvent was removed under reduced pressure, finally obtaining 6.3 g of 5-bromomethyl-2'-dioxyuridine (compound A) as a pale brown solid.

Preparation of Compound B

The compound A prepared in the above step was directly used in the next step without further purification, in consideration of its instability. Dimethylselenide (0.9 mL, 9.13 mmol) was placed into a 100 ml-volume round bottom flask and dissolved in 10 mL dry DMF added thereto. Then, $NaBH_4$ (760 mg, 20.1 mmol) was slowly added while blowing argon gas thereinto. At this time, the solution became clear with the generation of a hydrogen gas. After additional 10 minutes at an ambient for further reaction, 6.3 g of the compound A dissolved in 15 mL DMF was further added thereto via a syringe. The resulted reaction solution was stirred at an ambient for 12 hours. The DMF solvent was removed under reduced pressure, resulting in yellow oil as a residue which was then dissolved in ethyl acetate and washed with saturated $NaHCO_3$ (50 mL) three times. The resultant was finally washed with a saturated saline solution. The obtained organic phase was dried over anhydrous $Na_2SO_4$, and then the organic solvent was removed under reduced pressure. The residual yellow oil compound was purified by using a silica gel column chromatography, obtaining the compound B (3',5'-bis-O-acetyl 5-methylselenyl-methyl-2'-deoxy uridine) in the form of a white solid (2.7 g, 72%).

$^1$H NMR ($CDCl_3$) 9.41 (s, 1H), 7.43 (s, 1H), 6.28-6.32 (m, 1H), 5.19-5.21 (m, 1H), 4.24-4.41 (m, 3H), 3.44 (s, 2H), 2.47-2.52 (m, 1H), 2.11-2.13 (m, 7H), 2.02 (s, 3H); $^{13}$C-NMR ($CDCl_3$) 170.42, 170.28, 162.41, 150.06, 135.20, 113.82, 85.11, 82.33, 74.18, 63.88, 37.66, 20.96, 20.91, 19.30, 5.42; HRMS[MNa$^+$] calc. 443.0333. found 443.0327.

Example 1

Preparation of Compound 1

5-methylselenyl-methyl-2'-deoxy uridine) (MeSe-T)

The compound B (1.10 g, 1.26 mmol) was dissolved in 100 mL of a 1,4-dioxane/ammonium hydroxide (1:1 v/v) solution, and the mixture was stirred at an ambient for 12 hours. The solvent was removed under reduced pressure, and the residues were purified by a silica gel column chromatography, thereby obtaining Compound 1 in the form of a white solid (0.46 g, 95%).

$^1$H-NMR ($D_2O$) 7.82 (s, 1H), 6.27-6.30 (m, 1H), 4.44-4.48 (m, 1H), 4.02-4.05 (m, 1H), 3.74-3.86 (m, 2H), 3.46 (s, 2H), 2.36-2.41 (m, 2H), 1.95 (s, 3H); $^{13}$C-NMR ($D_2O$) 165.06, 152.18, 138.15, 113.97, 89.06, 86.54, 72.33, 62.89, 41.52, 20.07, 4.57; HRMS[MNa$^+$] calc. 359.0122. found 359.0111.

Example 2

Preparation of Compound 2

(5-isopropylselenyl-methyl-2'-deoxy uridine)

Compound 2 was prepared by using the same method as in the above example 1, except that diisopropyl diselenide was used instead of dimethyl diselenide.

$^1$H NMR (DMSO-$d_6$) 11.38 (s, 1H), 7.84 (s, 1H), 6.16 (m, 1H), 5.24 (m, 1H), 5.02 (m, 1H), 4.22 (m, 1H), 3.76-3.77 (m, 1H), 3.55 (m, 2H), 3.38 (m, 2H), 3.04 (m, 1H), 2.07 (m, 2H), 1.32-1.37 (m, 6H); $^{13}$C NMR (DMSO-$d_6$) 172.12, 163.11, 150.85, 136.91, 113.36, 88.03, 84.65, 71.14, 62.05, 29.92, 24.99, 23.19.

Example 3

Preparation of Compound 3

(5-cyclohexylselenyl-methyl-2'-deoxy uridine)

Compound 3 was prepared by using the same method as in the above example 1, except that dicyclohexyl diselanide was used instead of dimethyl diselenide.

$^1$H-NMR (DMSO-$d_6$) 11.38 (s, 1H), 7.83 (s, 1H), 6.17 (m, 1H), 5.25 (m, 1H), 5.03 (m, 1H), 4.22-4.26 (m, 1H), 3.76-3.79 (m, 1H), 3.52-3.61 (m, 2H), 3.15-3.17 (m, 1H), 2.83-2.90 (m, 1H), 2.02-2.12 (m, 2H), 1.93-1.96 (m, 2H), 1.59-1.65 (m, 3H), 1.53-1.55 (m, 1H), 1.36-1.44 (m, 1H), 1.21-1.33 (m, 4H); $^{13}$C-NMR (DMSO-$d_6$) 174.94, 162.83, 150.63, 136.56, 113.23, 87.81, 84.35, 70.96, 61.89, 34.53, 34.52, 26.73, 25.79, 22.94.

Example 4

Preparation of Compound 7

(5-phenylselenyl-methyl-2'-deoxy uridine) (PhSe-T)

Compound 7 was prepared by using the same method as in the above example 1, except that diphenyl diselanide was used instead of dimethyl diselenide.

$^1$H-NMR (DMSO-$d_6$) 11.42 (s, 1H), 7.54 (s, 1H), 7.47-7.25 (m, 5H), 6.08 (m, 1H), 5.22 (m, 1H), 4.96 (m, 2H), 4.00-4.10 (m, 2H), 3.77 (s, 2H), 3.70-3.73 (m, 1H), 1.87-2.00 (m, 1H), 1.70-1.75 (m, 1H); $^{13}$C-NMR ($CD_3OD$) 164.7, 151.9, 138.2, 136.1, 130.6, 130.4, 128.9, 113.0, 88.7, 86.0, 72.1, 62.8, 41.2, 24.0.

Test Example 1

Cytotoxicity Test on Cancer Cells

Human lung cancer cell line H460 was used in the present test. Firstly, the H460 cell line was cultured in RPMI 1640 medium with 100 U/mL of penicillin, 100 mg/mL of streptomycin and 10% FBS, under the condition of 37° C. and 5% $CO_2$ atmosphere. The cultured cells were placed on a 96-well-plate at the initial cell density of about $2 \times 10^3$ cells. In about 24 hours, the cells on the 96-well-plate were treated with the compound 1 and the compound 7 at a designated concentration for 48 hours. The relative cell viability was quantitatively determined by a colorimetric assay using a water-soluble tetrazolium salt. Optical density at 450 nm was measured by an automatic micro plate reader. The results were represented in FIGS. 1 and 2 in the drawings attached to the present specification.

Test Example 2

Radiosensitizing Effect Test

The cultured lung cancer cells H460 were treated with trypsin and then placed on a 60 mm plate at the density of about 500 cells. In about 24 hours, it was treated with PhSe-T or MeSe-T at the concentration of $IC_{20}$ and cultured for additional 24 hours. Next, the resulted culture was irradiated at various radiation doses (2, 4, 6, 8 Gy) by using Gammacell 3000 (radiation dose=3.2 Gy/min). After the irradiation, the cells were further cultured for 12 days. Colonies having a diameter of more than 0.5 mm were stained by 1% crystal violet solution, and then colonies including 50 or more cells were counted. The surviving fraction (SF) of cells was calculated by the following equation.

*SF*=the number of formed colony/the number of placed cells×plating efficiency(control)

Figure 3:
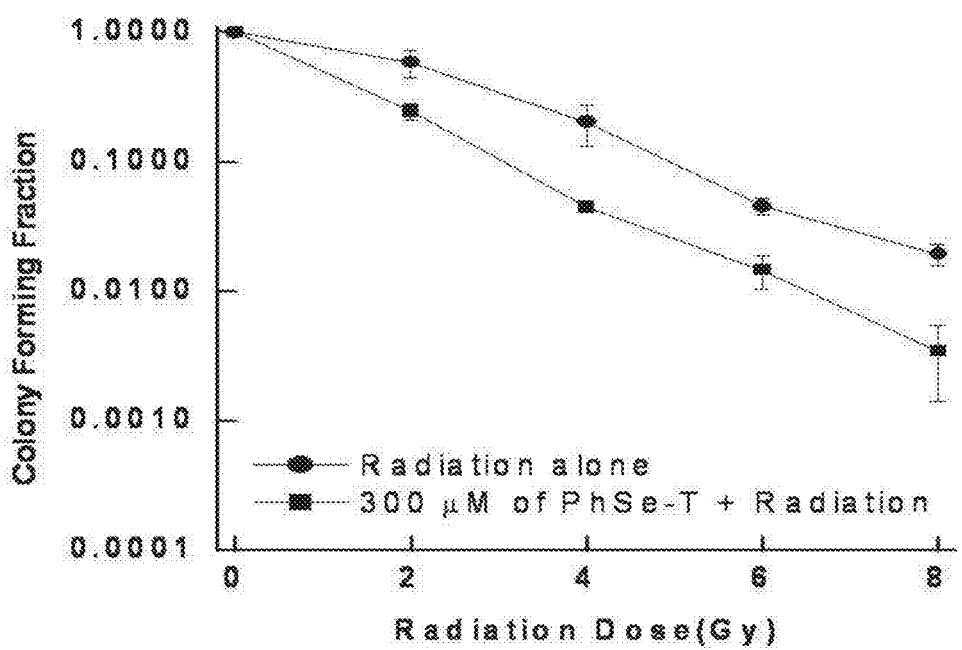
FIG. 3 is a plot showing the radiosensitizing effect of PhSe-T according to the present invention when exposed to radiation.
Figure 4:
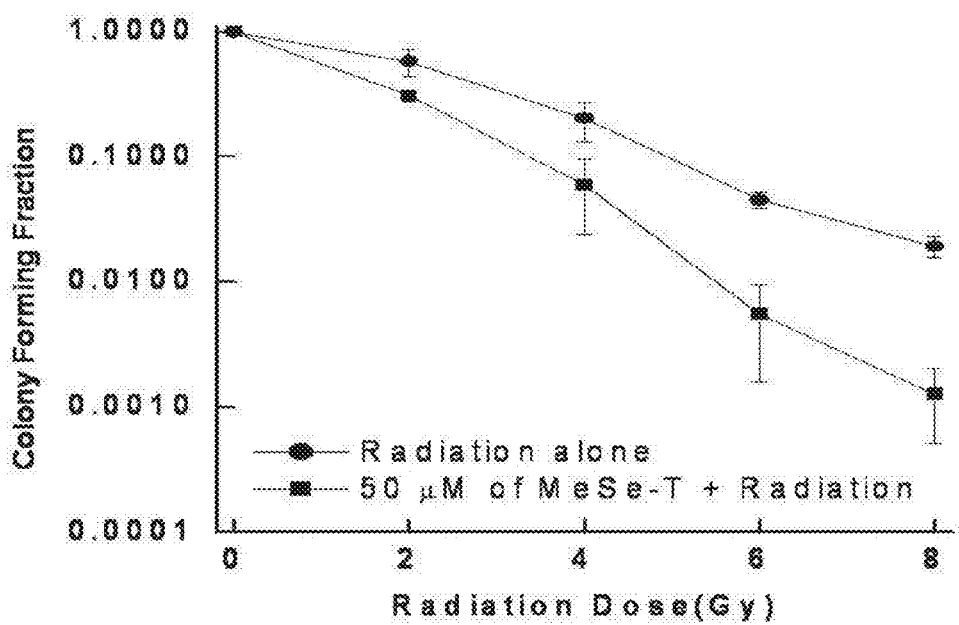
FIG. 4 is a plot showing the sensitizing effect of MeSe-T according to the present invention when exposed to radiation.

The results were represented in FIGS. 3 and 4.

The present inventors have revealed that novel 5-alkyl selenyl-methyluracil derivatives and 5-aryl selenyl-methyluracil derivatives represented by the above compounds 1 to 9 function as a radiosensitizer on lung cancer cell lines, for the first time. Regarding the compound 7, i.e., 5-phenylselenyl methyl dioxyuridine derivative, which is a well-known compound in this field of art, although it has been reported that DNA complementary bindings by photoreaction or gamma-ray are formed, when the compound 7 is independently introduced to a DNA double helix structure, its effect of enhancing radiotherapy on cancer cell lines has never been known so far.

Figure 2:
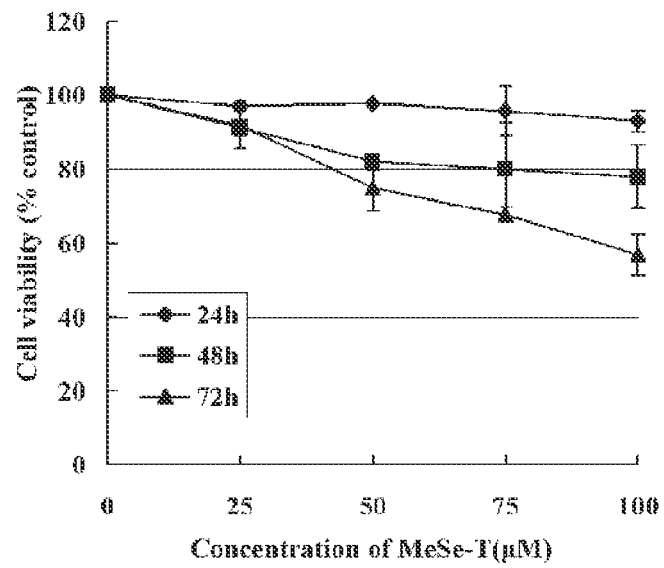
FIG. 2 is a plot showing the viability of lung cancer cell (H460) when treated by MeSe-T according to the present invention.

As shown in the test example 1, FIG. 1 and FIG. 2, the lung cancer cell line (H460) was treated with the compound 1 (MeSe-T), then after a lapse of 72 hours, $IC_{50}$ value thereof, that is the concentration where 50% cells are killed, were about 100 μM. The $IC_{50}$ value of the compound 7 (PhSe-T) was found to be about 500 μM. When the compound 1 or the compound 7 was applied alone to the cancer cell line, without the combined radiation treatment, it was found to have a weak cytotoxic effect.

Further, as shown in FIG. 3 and FIG. 4, when the compound prepared according to the present invention was applied together with radiation at the dose of around $IC_{20}$ value to cancer cells, death of the cancer cells significantly increased, as compared to the control group in which radiation treatment was applied alone without using said compounds of the present invention. Comparing to many reported conventional radiosensitizers which have serious side effects due to their intrinsic toxicity, it has been confirmed that the novel selenyl-methyluracil compounds developed by the present inventors have low toxicity of the compound per se as well as an excellent radiosensitizing effect in combined use with radiation, thereby promoting cancer cell death.

The invention claimed is:

1. A selenyl-methyluracil compound represented by the following chemical formula 1:

chemical formula 1

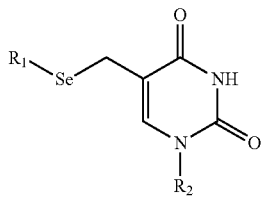

wherein $R_1$ is C1-C8 alkyl, C2-C7 alkenyl, C3-C6 cycloalkyl or C6-C12 aryl; $R_2$ is C1-C8 alkyl, carboxy (C6-C12)aryl, pentose or hexose; the alkyl, alkenyl, cycloalkyl or aryl group of $R_1$ may be further substituted with halogen, C1-C6 alkyl, C2-C7 alkenyl, C2-C7 alkylnyl, cyano, halogen, C1-C6 alkoxy, —$NR_{11}R_{12}$, carboxyl, nitro or hydroxyl group; wherein $R_{11}$ and $R_{12}$, being independent to each other, are hydrogen, C1-C6 alkyl, C6-C12 aryl or C3-C12 heteroaryl group containing at least one hetero atom selected from the group consisting of N, O and S; provided that the compound of which $R_1$ is phenyl and $R_2$ is

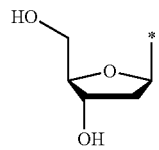

excluded.

2. The selenyl-methyluracil compound according to claim 1, which are represented by the following chemical formula 2:

chemical formula 2

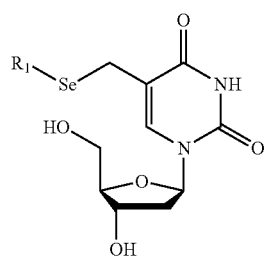

wherein $R_1$ is C1-C6 alkyl, C2-C7 alkenyl, or C3-C6 cycloalkyl; the alkyl, alkenyl or cycloalkyl group of $R_1$ may be further substituted with halogen, C1-C6 alkyl, C2-C7 alkenyl, C2-C7 alkylnyl, cyano, halogens, C1-C6 alkoxy, —$NR_{11}R_{12}$, carboxyl, nitro or hydroxyl group; wherein $R_{11}$ and $R_{12}$, being independent from each other, are hydrogen, C1-C6 alkyl, C6-C12 aryl or C3-C12 heteroaryl group containing at least one heteroatom selected from N, O and S.

3. The selenyl-methyluracil compound according to claim 2, which is selected from the group consisting of compounds represented by the following chemical formulas:

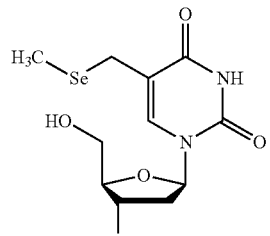

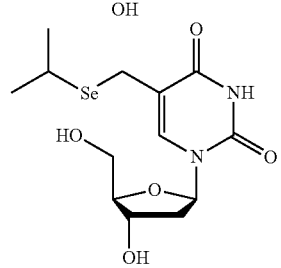

-continued

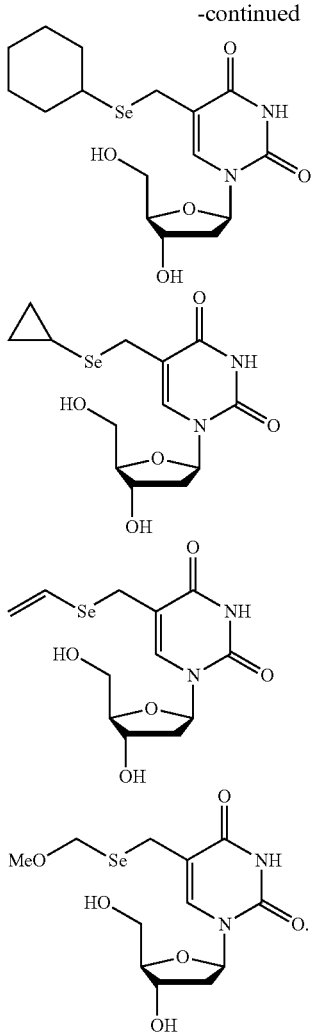

4. A pharmaceutical composition comprising a selenyl-methyluracil compound represented by the following chemical formula 3 or a pharmaceutically acceptable salt thereof as an active ingredient:

chemical formula 3

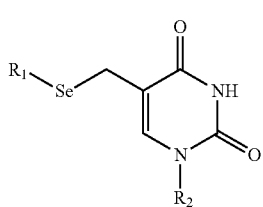

wherein $R_1$ is C1-C8 alkyl, C2-C7 alkenyl, C3-C6 cycloalkyl, C6-C12 aryl or C3-C12 heteroaryl group containing at least one heteroatom selected from N, O and S; $R_2$ is C1-C8 alkyl, carboxy(C6-C12)aryl, pentose or hexose; the alkyl, alkenyl, cycloalkyl, aryl or heteroaryl group of $R_1$ may be further substituted with halogen, C1-C6 alkyl, C2-C7 alkenyl, C2-C7 alkylnyl, cyano, halogen, C1-C6 alkoxy, —$NR_{11}R_{12}$, carboxyl, nitro or hydroxyl group; wherein $R_{11}$ and $R_{12}$, being independent from each other, are hydrogen, C1-C6 alkyl, C6-C12 aryl or C3-C12 heteroaryl group containing at least one heteroatom selected from N, O, and S, provided that a compound wherein $R_1$ is phenyl and $R_2$

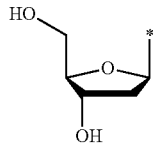

is excluded.

5. The pharmaceutical composition according to claim 4, wherein the selenyl-methyluracil compound is represented by the following chemical formulas 4 or 5:

chemical formula 4

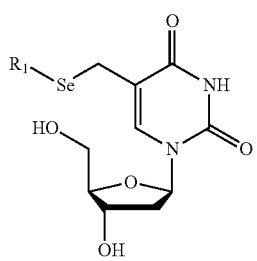

chemical formula 5

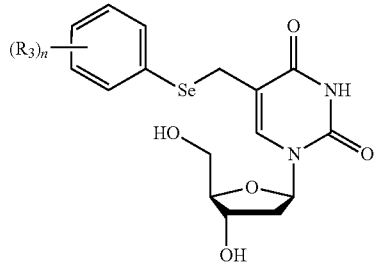

wherein $R_1$ is C1-C6 alkyl, C2-C7 alkenyl or C3-C6 cycloalkyl; the alkyl, alkenyl or cycloalkyl group of $R_1$ may be further substituted with halogen, C1-C6 alkyl, C2-C7 alkenyl, C2-C7 alkylnyl, cyano, halogen, C1-C6 alkoxy, —$NR_{11}R_{12}$, carboxyl, nitro or hydroxyl group; wherein $R_{11}$ and $R_{12}$, being independent from each other, are hydrogen, C1-C6 alkyl, C6-C12 aryl or C3-C12 heteroaryl group containing at least one heteroatom selected from N, O and S; $R_3$ is halogen, C1-C6 alkyl, C2-C7 alkenyl, C2-C7 alkynyl, cyano, halogen, C1-C6 alkoxy, —$NR_{21}R_{22}$, carboxyl, nitro or hydroxyl group; wherein $R_{21}$ and $R_{22}$, being independent from each other, are hydrogen, C1-C6 alkyl, C6-C12 aryl or C3-C12 heteroaryl group containing at least one heteroatom selected from N, O, and S; and n is an integer of 1 to 5.

6. The pharmaceutical composition according to claim 5, wherein the selenyl-methyluracil compound is selected from the group consisting of the following compounds:

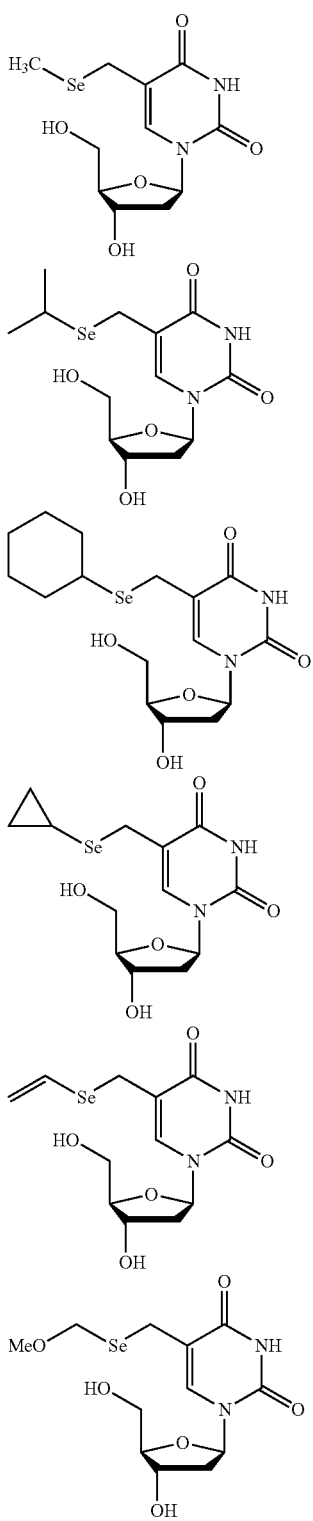

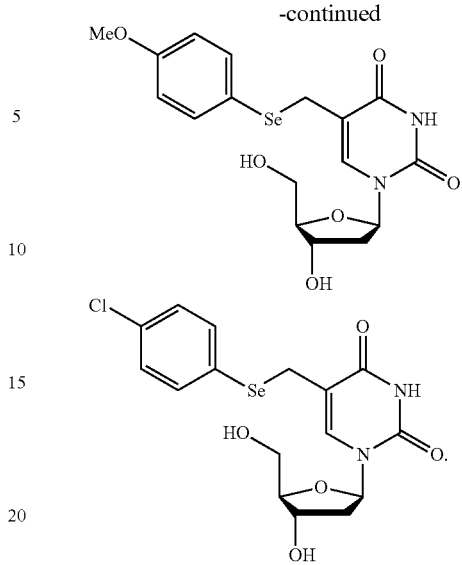

7. A method for enhancing a radiation treatment of a subject, comprising administering the pharmaceutical composition of claim 4 to the subject before or after the radiation treatment.

8. A method for enhancing a radiation treatment of a subject, comprising administering the pharmaceutical composition of claim 5 to the subject before or after the radiation treatment.

9. A method for enhancing a radiation treatment of a subject, comprising administering the pharmaceutical composition of claim 6 to the subject before or after the radiation treatment.

10. A method for treating a cancer, which comprises administering the pharmaceutical composition of claim 4 in an effective amount to a subject in need thereof.

11. The method according to claim 10, wherein the cancer is prostate cancer, breast cancer, brain tumor, thyroid cancer, pancreatic cancer, pituitary cancer, cervical cancer, uterine cancer, ovarian cancer, esophageal cancer, gastric cancer, colon cancer, rectal cancer, liver cancer, gallbladder cancer, lung cancer, oral cavity cancer, skin cancer, renal cancer, leukemia, lymphoma and myeloma.

12. A method for treating a cancer, which comprises administering the pharmaceutical composition of claim 5 in an effective amount to a subject in need thereof.

13. A method for treating a cancer, which comprises administering the pharmaceutical composition of claim 6 in an effective amount to a subject in need thereof.

14. The method according to claim 7, wherein the radiation treatment is a radiation treatment of a cancer and the subject is a cancer patient.

* * * * *